(12) United States Patent
Panchaud-Mirabel

(10) Patent No.: US 7,906,335 B2
(45) Date of Patent: Mar. 15, 2011

(54) CULTURE MEDIUM FOR THE PRODUCTION OF FILAMENTARY FUNGI

(75) Inventor: Elisabeth Panchaud-Mirabel, Toulouse (FR)

(73) Assignee: Urea Casale S.A. (CH)

( * ) Notice: Subject to any disclaimer, the term of this patent is extended or adjusted under 35 U.S.C. 154(b) by 625 days.

(21) Appl. No.: 10/597,897

(22) PCT Filed: Feb. 8, 2005

(86) PCT No.: PCT/EP2005/001262
§ 371 (c)(1),
(2), (4) Date: May 31, 2007

(87) PCT Pub. No.: WO2005/078067
PCT Pub. Date: Aug. 25, 2005

(65) Prior Publication Data
US 2008/0096265 A1    Apr. 24, 2008

(30) Foreign Application Priority Data
Feb. 11, 2004    (EP) .................................... 04003036

(51) Int. Cl.
C12N 5/00 (2006.01)
C12N 5/02 (2006.01)
(52) U.S. Cl. ........................................................ 435/430
(58) Field of Classification Search .................. 435/430
See application file for complete search history.

(56) References Cited

U.S. PATENT DOCUMENTS

| | | | | |
|---|---|---|---|---|
| 3,625,826 A | * | 12/1971 | Kobayashi et al. | 435/142 |
| 3,992,262 A | * | 11/1976 | Shieh | 435/234 |
| 5,643,775 A | * | 7/1997 | Takahashi et al. | 435/193 |
| 2004/0072325 A1 | | 4/2004 | Anazawa et al. | |

FOREIGN PATENT DOCUMENTS

| | | |
|---|---|---|
| EP | 1050219 A | 11/2000 |
| WO | WO 88/06407 | 9/1988 |
| WO | 91/13887 A1 | 9/1991 |

OTHER PUBLICATIONS

Hatzinikolaou et al. Factors regulating production of glucose oxidase by *Aspergillis niger*. Enzyme and Microbial Technology 17: 530-534 1995.*
McCoy, et al., "A Simplified Medium for the Production of *Hirsutella thompsonii*", Journal of Invertebrate Pathology, 31:137-139 (1978).
Liu, et al., "Nutritional Requirements of the Nematophagous Fungus *Hirsutella rhossiliensis*", Biocontrol Science and Technology, 12:381-393 (2002).
Bastos, "Effect of Temperature, pH and Nutrition on Growth and Sporulation of *Trichoderma stromaticum* sp. nov., an Antagonist of Cocoa Witches' Broom Pathogen", Summa Phytopanthologica, 27(1):73-77 (2001).
Cayrol, et al., "La lutte Biologique Contres les Nematodes Phyytoparasites", Le Courtier De La Cellule Environment, Online 17:1-14 (1992).
Nishikawa, "Biochemistry of Filamentous Fungi, I.", Bulletin of the Agricultural Chemical Society of Japan. 1932, vol. 8, pp. 1007-1015.
Ikram-Ul-Haq et al., "Nitrogen Requirement for Enhanced Citric Acid Production by Filamentous Fungi *Aspergillus Niger*", Sci. Int., 2002, vol. 14, No. 4, pp. 329-332.

* cited by examiner

*Primary Examiner* — Wendy Haas
(74) *Attorney, Agent, or Firm* — Akerman Senterfitt

(57) ABSTRACT

A culture medium for filamentary fungi comprising at least one carbon source chosen from the group consisting of molasses, malt extract and sucrose and at least one organic nitrogen source chosen from yeast extract and corn steep liquor is described; a method for producing filamentary fungi, in particular nematophagus fungi on an industrial scale, comprising the step of seeding conidia of such fungi in the aforementioned culture medium and maintaining such a culture medium at a temperature of 23-30° C. for a time of 5-10 days to determine the reproduction and growth of the fungi is also described.

4 Claims, No Drawings

CULTURE MEDIUM FOR THE PRODUCTION OF FILAMENTARY FUNGI

FIELD OF APPLICATION

The present invention concerns the technical field of phytosanitary agents.

In particular, the invention refers to a culture medium for filamentary fungi, more specifically for nematophagus fungi.

PRIOR ART

The use of micro-organisms and in particular fungi as phytosanitary agents constitutes an increasingly common practice.

Fungi-based products are already marketed for the fight against insects, phytopathogenic fungi and other parasites typical of farming crops.

For example, in patent U.S. Pat. No. 5,811,092 nematophagus agents are described for fighting nematodes of the genera *Meloidogyne, Hetherodera* and *Ditylenchus*, consisting of particular strains of *Arthrobotrys conoides Dreschsler*, a filamentary fungus.

The aforementioned nematodes are responsible for serious vegetable and fungus diseases and cause huge economic losses, as they lead to 50-70% of the harvest being compromised.

The use of nematophagus fungi, as an alternative to conventional anti-parasitic chemicals (for example methyl bromide, trichloronitromethane, dichloropropene, etc.) for application to the soil prior to its cultivation or to carbamates applied directly to the crops, allows serious problems, such as sterilization of the soil, destruction of the ecological balance and potential toxicity to man and animals, to be avoided.

Nematophagus fungi are thus particularly suitable for use in organic farming but still have a rather high cost, as a result of the difficulties in producing them industrially at high yields.

There is, therefore, a need to make cheaper nematophagus fungi available for use in agriculture.

The problem at the basis of the present invention was that of providing a culture medium for filamentary fungi and in particular for nematophagus fungi, that allows such microorganisms to be produced at industrial level at high yields and in short periods of time, with a consequent decrease in the cost of the end product.

SUMMARY OF THE INVENTION

Such a problem has been solved, according to the invention, by a culture medium for filamentary fungi comprising at least one carbon source chosen from the group consisting of molasses, malt extract and sucrose and at least one organic nitrogen source chosen between yeast extract and corn steep liquor.

Preferably, the aforementioned at least one carbon source constitutes 70 to 85% by weight of the dry weight of the culture medium and the aforementioned at least one organic nitrogen source constitutes 15 to 30% by weight of the dry weight of the culture medium.

The culture medium according to the present invention can also include a mineral nitrogen source, consisting of ammonium nitrates or salts. The aforementioned mineral nitrogen source is usually added gradually to the culture medium during growth of the fungi in an amount not greater than 10% by weight of the dry weight of the culture medium and usually between 5 and 8% by weight.

A preferred composition of culture medium of the present invention consists of 75-85% malt extract and 15-25% yeast extract (the percentages are, as in the rest of the present description, by weight of the dry weight of the culture medium).

Another preferred culture medium according to the invention comprises 60-65% molasses, 10-15% sucrose, 10-15% corn steep liquor and 10-15% yeast extract. Advantageously, such a culture medium contains, in addition, 5 to 8% of a mineral nitrogen source, in particular diammonium hydrogen phosphate.

A further preferred culture medium according to the present invention contains two carbon sources, i.e. malt extract, in the amount of 25-30%, and molasses, in the amount of 40-45%, as well as corn steep liquor, in the amount of 25-30%.

DETAILED DESCRIPTION OF THE INVENTION

The present invention shall be further described with reference to some example embodiments provided for illustrative and not for limiting purposes.

Before proceeding with the illustration of the examples, we consider it helpful to provide some specifications regarding the components of the culture medium according to the invention.

Malt extract and/or molasses and/or sucrose are used as carbon sources.

The malt extract is obtained by germination of cereal grains (generally barley). At germination, specific enzymes (amylases) are produced, which allow the conversion of the starch into sugars. The malt extract contains about 60% maltose, vitamins and numerous micronutrients.

Molasses constitutes a by-product of the sugar industry and comes in the form of a black-brownish viscous liquid, containing 10% water, 35% sucrose, 20% other sugars and 15% ash.

Yeast extract and corn steep liquor are used as organic nitrogen sources.

The yeast extract is obtained by autolysis of *Saccharomyces cerevisiae* and comes in the form of fine pale yellow powder, easily soluble in water. The yeast extract contains peptides, free amino acids, purine and pyrimidine bases, as well as water-soluble vitamins of the B-group. The yeast extract has a total nitrogen content of 10% and a α-amminic nitrogen content of 5%.

The corn steep liquor is obtained through steeping of corn grains at 50° C. for 24-48 hours in water containing sulphur dioxide. This reagent allows the proteic network surrounding the starch grains to be destructured and offers the advantage of preventing the development of undesirable micro-organisms during steeping. The corn steep liquor has a total nitrogen content of 7% and a α-amminic nitrogen content of 1.7% and also contains 5% sugars, 4% potassium, 3% phosphorus and 17% different minerals.

Various culture media based upon the carbon and nitrogen sources mentioned above have been tested. These media can be classified in the following three classes:

class 1: media having malt extract as the main carbon source;
class 2: media having molasses as the main carbon source;
class 3: media in which the main carbon source consists of malt extract and molasses.

The percentage content of the organic nitrogen source of the media according to the invention can be decreased, replacing part of such organic nitrogen source with an inorganic nitrogen source (ammonium nitrates or compounds), which is added gradually in small amounts during culturing.

This addition of inorganic nitrogen during culturing allows better nutrition of the micro-organism and, in the case of filamentary fungi, strengthening of the mycelial filaments.

Replacement of part of the organic nitrogen source with an inorganic nitrogen source also has the advantage of reducing the production costs, as the organic nitrogen sources (yeast extract and corn steep liquor) constitute the most expensive components of the culture medium according to the invention.

The culture medium according to the invention is particularly suitable for use in the production of filamentary fungi of the Moniliales family. In particular, in the examples indicated below, filamentary fungi of *Arthrobotrys conoides Dreschsler* were used.

Example 1

This concerns a class 1 culture medium.

The growth of filamentary fungi was carried out in a 300 ml Erlen flask, containing 150 ml of culture medium.

The medium consisted of 20 g/l of malt extract and 4 g/l of yeast extract and was sterilized prior to seeding with conidia of the fungus in question.

The culturing lasted for 6 days from seeding at a temperature of about 27° C.

From the third day onwards, samples were taken from the culture medium to determine the dry mass (g/l) and the number of propagules (CFU/l). To determine the dry mass, 20 ml of the culture medium were filtered and then dried out in an oven at 100° C. for 24 hours. The number of propagules was determined on 1 ml of culture medium.

A summary of the results obtained is shown in Table 1, as follows.

TABLE 1

| day | pH | Dry mass (g/l) | CFU/l |
| --- | --- | --- | --- |
| 0 | 6 | 0 | 0.00 |
| 3 | 5.26 | 1.505 | $1.92 \cdot 10^8$ |
| 4 | 5.79 | 3.345 | $1.30 \cdot 10^9$ |
| 5 | 6.56 | 5.05 | $3.07 \cdot 10^9$ |
| 6 | 6.11 | 9.895 | $4.43 \cdot 10^9$ |

Example 2

The test carried out in example 1 was repeated in a 2 liter mini-reactor containing 1.2 liters of the culture medium as in example 1. The experimental conditions were the same as in example 1, with the only difference that the sampling began the day after the seeding of the conidia.

The mini-reactor in question is a container with a rounded bottom, provided with a blade agitator, heating and cooling means, air blowing means, as well as probes for pH, $O_2$ and temperature detection.

A summary of the results obtained is shown in Table 2, as follows.

TABLE 2

| Day | pH | Dry mass (g/l) | CFU/l |
| --- | --- | --- | --- |
| 0 | 6 | 0 | 0.00 |
| 1 | 5.51 | 1.175 | $2.50 \cdot 10^6$ |

TABLE 2-continued

| Day | pH | Dry mass (g/l) | CFU/l |
| --- | --- | --- | --- |
| 2 | 5.5 | 1.3825 | $1.80 \cdot 10^7$ |
| 3 | 6.61 | 1.59 | $8.50 \cdot 10^7$ |
| 4 | 5.4 | 4.03 | $9.60 \cdot 10^8$ |
| 5 | 5.13 | 4.29 | $1.27 \cdot 10^9$ |
| 6 | 5.08 | 5.625 | $3.10 \cdot 10^9$ |
| 7 | 5.5 | 7.848 | $6.08 \cdot 10^9$ |

At the end of seven days of culturing almost 8 grams of fungi per liter of culture medium are thus obtained with $6.08 \cdot 10^9$ propagules.

Example 3

This concerns a test carried out with a class 2 culture medium.

The culture of the filamentary fungus was carried out in a 300 ml Erlen flask, containing 150 ml of culture medium.

The medium consisted of 25 g/l of molasses, 5 g/l of sucrose, 5 g/l of corn steep liquor and 5 g/l of yeast extract and was sterilized prior to seeding with conidia of the fungus in question.

The culture was incubated for 6 days from seeding at a temperature of about 27° C.

From the third day onwards, samples were taken from the culture medium to determine the dry mass (g/l) and the number of propagules (CFU/l). To determine the dry mass, 20 ml of the culture medium were filtered and then dried out in an oven at 100° C. for 24 hours. The number of propagules was determined on 1 ml of culture medium.

A summary of the results obtained is shown in Table 3, as follows.

TABLE 3

| day | pH | Dry mass (g/l) | CFU/l |
| --- | --- | --- | --- |
| 0 | 5.07 | 0 | 0.00 |
| 3 | 4.87 | 1.58 | $3.12 \cdot 10^7$ |
| 4 | 4.20 | 3.82 | $1.40 \cdot 10^8$ |
| 5 | 6.46 | 6.76 | $1.30 \cdot 10^9$ |
| 6 | 6.98 | 9.995 | $3.65 \cdot 10^9$ |

Example 4

The test carried out in example 3 was repeated in a 2 liter mini-reactor as described in example 2, containing 1.2 liters of the culture medium as in example 3. The experimental conditions were the same as in example 3, with the only difference that the sampling began the day after the seeding of the conidia.

A summary of the results obtained is shown in Table 4, as follows.

TABLE 4

| Day | pH | Dry mass (g/l) | CFU/l |
| --- | --- | --- | --- |
| 0 | 5.07 | 0 | 0.00 |
| 1 | 5.04 | 2.675 | $9.90 \cdot 10^7$ |
| 2 | 5.01 | 3.9 | $3.00 \cdot 10^8$ |
| 3 | 5.44 | 5.125 | $5.00 \cdot 10^8$ |
| 4 | 6.11 | 8.295 | $8.20 \cdot 10^8$ |
| 5 | 6.69 | 2.75 | $1.07 \cdot 10^9$ |

TABLE 4-continued

| Day | pH | Dry mass (g/l) | CFU/l |
|---|---|---|---|
| 6 | 7.32 | 3.485 | $2.10 \cdot 10^9$ |
| 7 | 7.65 | 10.164 | $3.77 \cdot 10^9$ |

The results shown for the days from the fifth onwards may appear anomalous but this is only due to an excessive concentration of fungi in the culture medium, which no longer allows homogeneous samples to be taken.

The last sample was taken directly from the reactor.

In this case, in seven days, more than 10 grams of fungi per liter of culture medium are obtained with a propagule content of $3.77 \cdot 10^9$.

Example 5

This concerns a test realized with a class 3 culture medium.

The culture of the filamentary fungus was carried out in a 300 ml Erlen flask, containing 150 ml of culture medium.

The medium consisted of 15 g/l of molasses, 10 g/l of malt extract and 10 g/l of corn steep liquor and was sterilized prior to seeding with conidia of the fungus in question.

The culture was incubated for 6 days from seeding at a temperature of about 27° C.

From the third day onwards, samples were taken from the culture medium to determine the dry mass (g/l) and the number of propagules (CFU/l). To determine the dry mass, 20 ml of the culture medium were filtered and then dried out in an oven at 100° C. for 24 hours. The number of propagules was determined on 1 ml of culture medium.

A summary of the results obtained is shown in Table 5, as follows.

TABLE 5

| day | pH | Dry mass (g/l) | CFU/l |
|---|---|---|---|
| 0 | 4.7 | 0 | 0.00 |
| 3 | 4.49 | 1.82 | $2.38 \cdot 10^7$ |
| 4 | 4.62 | 3.815 | $1.78 \cdot 10^8$ |
| 5 | 5.25 | 5.57 | $1.23 \cdot 10^9$ |
| 6 | 6.03 | 8.555 | $1.35 \cdot 10^9$ |

Example 6

The test carried out in example 5 was repeated in a 2 liter mini-reactor as described in example 2, containing 1.2 liters of the culture medium as in example 5. The experimental conditions were the same as in example 5, with the only difference that the sampling began the day after the seeding of the conidia.

A summary of the results obtained is shown in Table 6, as follows.

TABLE 6

| Day | pH | Dry mass (g/l) | CFU/l |
|---|---|---|---|
| 0 | 4.7 | 0 | 0.00 |
| 1 | 4.61 | 2.905 | $5.60 \cdot 10^6$ |
| 2 | 4.7 | 3.085 | $6.00 \cdot 10^7$ |
| 3 | 4.56 | 3.265 | $1.23 \cdot 10^8$ |
| 4 | 6.11 | 5.295 | $3.20 \cdot 10^8$ |
| 5 | 5.99 | 5.88 | $7.00 \cdot 10^8$ |
| 6 | 6.94 | 6.305 | $9.50 \cdot 10^8$ |
| 7 | 7 | 10.026 | $2.22 \cdot 10^9$ |

In seven days, more than 10 grams of fungi per liter of culture medium were obtained with a propagule content of $2.22 \cdot 10^9$.

Example 7

The culture medium of example 3 was modified as follows, so as to reduce the content of the two organic nitrogen sources, which constitute the most expensive components:
25 g/1 molasses;
5 g/l sucrose;
2.5 g/l corn steep liquor;
2.5 g/l yeast extract.

With such culture medium, a culture test (A), using the aforementioned fungus, was carried out for comparison with another two culture tests (B and C), in which the same culture medium was used and which involved subsequent additions of a mineral nitrogen source from the fourth day onwards.

In test B, 0.21 g of diammonium hydrogen phosphate were added three times from the fourth day (more precisely on the fourth, sixth and eighth day), for a total addition of 0.63 g, and in test C 0.28 g were added three times, again from the fourth day (more precisely on the fourth, sixth and eighth day), for a total addition of 0.84 g.

The tests were conducted in 500 ml Erlen flasks, containing 300 ml of culture medium, sterilized before the seeding of the conidia.

On the ninth and last day of culture, the total nitrogen content of the culture medium as such (A) was equal to 0.85 g/l whereas in the media added with diammonium hydrogen phosphate (A and B) it was equal to 1.05 g/l (A) and 1.26 g/l (B), respectively.

From the third day onwards, samples from the culture media were taken every two days to determine the dry mass (g/l) and the number of propagules (CFU/l). To determine the dry mass, 20 ml of the culture medium were filtered and then dried out in an oven at 100° C. for 24 hours. The number of propagules was determined on 1 ml of culture medium.

A summary of the results obtained is shown in Table 7, as follows.

TABLE 7

| Day | A pH | A MS | A CFU | B pH | B MS | B CFU | C pH | C MS | C CFU |
|---|---|---|---|---|---|---|---|---|---|
| 0 | 5.06 | 0.00 | 0.00 | 5.06 | 0.00 | 0.00 | 5.09 | 0.00 | 0.00 |
| 3 | 4.92 | 3.94 | $5.50 \cdot 10^6$ | 4.80 | 2.84 | $2.50 \cdot 10^4$ | 4.80 | 3.36 | $2.50 \cdot 10^4$ |
| 5 | 5.12 | 3.44 | $1.75 \cdot 10^8$ | 4.89 | 4.57 | $4.73 \cdot 10^8$ | 5.30 | 3.48 | $3.05 \cdot 10^8$ |

TABLE 7-continued

| Day | A pH | A MS | A CFU | B pH | B MS | B CFU | C pH | C MS | C CFU |
|---|---|---|---|---|---|---|---|---|---|
| 7 | 6.68 | 6.45 | $1.58 \cdot 10^9$ | 5.47 | 8.32 | $3.15 \cdot 10^9$ | 6.39 | 5.48 | $4.00 \cdot 10^9$ |
| 9 | 7.14 | 8.63 | $3.20 \cdot 10^9$ | 5.44 | 11.30 | $7.25 \cdot 10^9$ | 5.86 | 7.86 | $6.78 \cdot 10^9$ |

MS = dry mass (g/l).
CFU = propagules/liter.

As it can be seen from the table shown above, the addition of a mineral nitrogen source, especially when in small amount (test B), allows a considerable increase in dry mass to be obtained starting on the seventh day of culturing and a more than 100% increase in the number of propagules to be obtained for the same culturing time.

The invention claimed is:

1. A culture medium for filamentary fungi comprising
   60-65% molasses,
   10-15% sucrose,
   10-15% corn steep liquor and
   10-15% yeast extract.

2. A culture medium according to claim 1, further comprising 5 to 8% of a mineral nitrogen source.

3. A culture medium according to claim 2, wherein said mineral nitrogen source consists of diammonium hydrogen phosphate.

4. A method for producing filamentary fungi, in particular nematophagus fungi, on an industrial scale, comprising the step of seeding conidia of said fungi in a culture medium according to claim 1 and keeping said culture medium at a temperature of 23-30° C. for a time of 5-10 days to determine the reproduction and growth of the fungi.

* * * * *